United States Patent

Schroeppel

Patent Number: 5,190,052
Date of Patent: Mar. 2, 1993

[54] PACER LEAD WITH BIPOLAR ELECTRODE

[75] Inventor: Edward A. Schroeppel, Lake Jackson, Tex.

[73] Assignee: Intermedics, Inc., Angleton, Tex.

[21] Appl. No.: 616,794

[22] Filed: Nov. 21, 1990

[51] Int. Cl.$^5$ ............................................. A61N 1/05
[52] U.S. Cl. ................................. 128/786; 128/419 P; 128/642
[58] Field of Search ............ 128/784, 785, 786, 419 P, 128/642

[56] References Cited

U.S. PATENT DOCUMENTS

| | | | |
|---|---|---|---|
| 4,662,377 | 5/1987 | Heilman et al. | 128/419 D |
| 4,825,871 | 5/1989 | Cansell | 128/786 |
| 5,010,894 | 4/1991 | Edhag | 128/786 |

FOREIGN PATENT DOCUMENTS 0024913 8/1979 European Pat. Off.
0009732 9/1979 European Pat. Off.

Primary Examiner—William E. Kamm
Assistant Examiner—Scott M. Getzow
Attorney, Agent, or Firm—John R. Merkling

[57] ABSTRACT

A bipolar sensing lead for use with an implantable device, particularly a cardiac pacemaker, comprising a first sensing electrode located adjacent an outer surface of the lead and a second sensing electrode spaced away from that surface in at least two non-linear directions. In a preferred embodiment, the first sensing electrode is a ring electrode at the outer surface of the lead. The second sensing electrode comprises a conductive ring around the circumference of a collapsible, flexible disk.

15 Claims, 5 Drawing Sheets

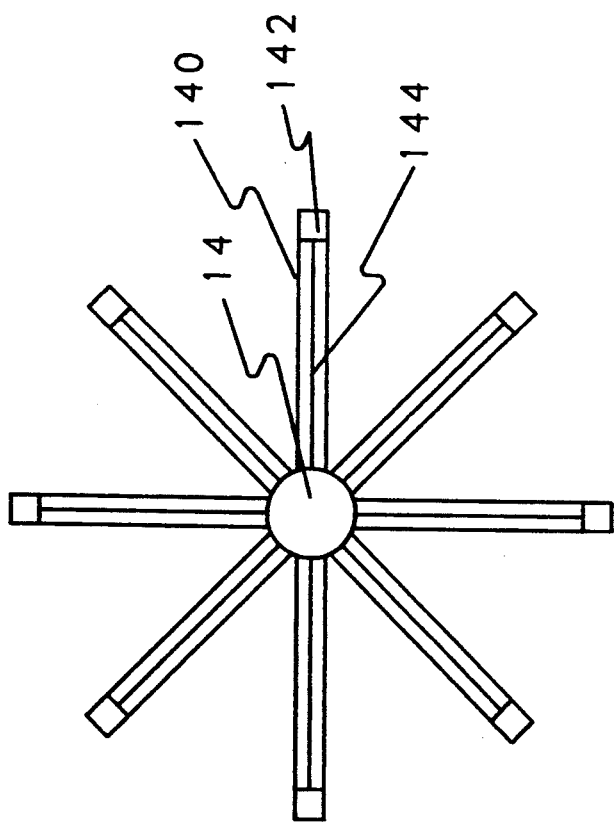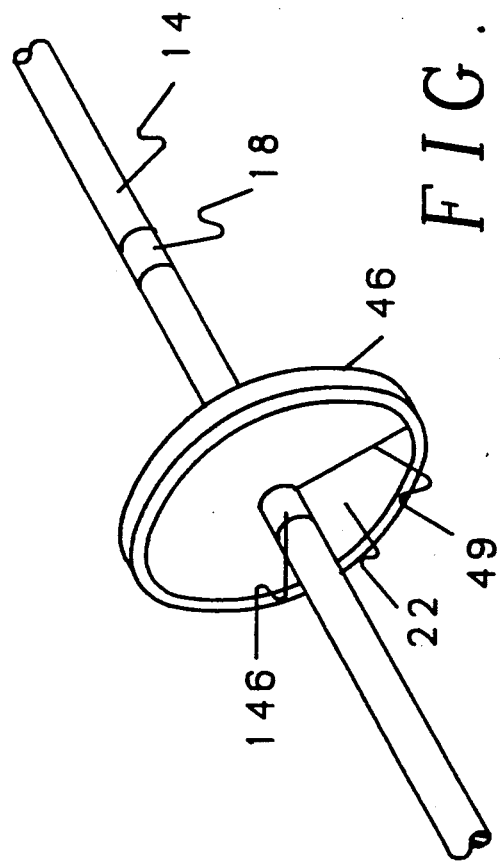

PACER LEAD WITH BIPOLAR ELECTRODE

FIELD OF MY INVENTION

My invention relates to leads for implantable therapeutic devices, and in particular to leads for implantable cardiac pacemakers. More specifically, my invention is related to bipolar leads for cardiac pacemakers adapted to sense electrical phenomena in the heart.

BACKGROUND OF MY INVENTION

Cardiac pacemakers stimulate the heart with electrical impulses to induce a heart beat. Pacemakers may also sense the condition of the heart so that stimuli may be applied in an appropriate manner. In certain situations it is appropriate to sense the electrical condition of the atrium of the heart in order to stimulate the ventricle. For this purpose, a cardiac pacemaker may be provided with two leads, one terminating at a stimulating electrode in the ventricle and a second terminating at a sense electrode in the atrium.

Such combinations of cardiac pacemakers and leads can both sense in the atrium and stimulate in the ventricle. The requirement, however, that two leads be used increases the complexity of implantation and requires that an additional lead be passed through a vein into the heart. The configuration, therefore, increases resistance to the flow of blood in the circulatory system of the patient. To overcome these drawbacks, leads with bipolar sense electrodes have been proposed. These leads have both the stimulating and sensing electrodes on the same lead. The sense electrode in the atrium, however, can generally not be attached to an inner surface of the heart. Consequently, the electrical condition of the heart is sensed through the blood, rather than at a muscle wall. Moreover, the position of the electrode with respect to the walls of the heart can shift so that the sensed condition is affected not only by the electrical status of the heart, but also by the position of the sense electrode from cycle to cycle. Finally, since the electrical muscle stimuli in the atrium are generally weaker than those which occur in the ventricle, electrical changes in the ventricle, detected at the sense electrode in the atrium, may be misinterpreted as representing the electrical condition of the atrium.

To address these limitations of single pass lead systems, leads with bipolar sense electrodes and so-called orthogonal sensing, have been proposed. Bipolar electrode configurations are recognized as being beneficial in cancelling out noise and muscle artifacts and far-field interference in general. They comprise a lead having two electrodes available for sensing. One such configuration has been disclosed by Goldreyer in U.S. Pat. No. 4,365,639. Goldreyer placed several electrodes circumferentially and substantially equidistantly from a distal tip of a lead. Each electrode was connected through a conductor to the cardiac pacemaker. The basic premise for the sensing electrodes in Goldreyer was that an electrical wavefront, propagating through the heart, would reach one electrode slightly before the second electrode. The electrical difference between potentials at the two electrodes and the variation in that difference over time could be used in the pacemaker to identify and detect a wavefront. Goldreyer's electrodes, however, are relatively small and set very close together, being separated by, at most, a diameter of a lead. As will be explained more fully below, the efficiency of bipolar sensing electrodes depends, in part, on the distance between the electrodes. When an electrical wavefront sweeps through the heart, there is usually a region of negative potential followed by region of positive potential, each region having a local maximum. The greatest difference in potential would be detected if, by chance, the negative maximum reached an electrode just as the positive maximum reached another electrode. Given the close spacing of the Goldreyer electrode, it is unlikely that the maxima would reach different electrodes simultaneously. Moreover, a bipolar electrode is sensitive to the direction of propagation of an approaching wavefront. For example, imagine two electrodes connected to a suitable cardiac pacemaker. If a wavefront approaches the two electrodes, along a line connecting the two electrodes, the wavefront will reach the first electrode before it will reach the other electrode. Measurement of an electrical potential difference as the wavefront passes over the two electrodes is possible. If, however, the wavefront approaches the electrodes from a direction perpendicular to the line connecting the two electrodes, the wavefront would reach the two electrodes simultaneously. However large the wavefront might be in absolute terms, there would be no difference in the electrical potential of the two electrodes and, therefore, the wavefront would not be detected.

Some of these problems were addressed by Robert Brownlee in U.S. Pat. No. 4,962,767. Brownlee designed a lead or catheter having bipolar electrodes positioned on opposite sides of the lead and being spaced from one another along the axis of the lead. Brownlee noted that it would be preferable to locate both the bipolar electrodes adjacent a cardiac wall, as the electrical waves could be expected to be more intense closer to the cardiac wall. Such a fortuitous circumstance, however, could not be guaranteed in the placement of the lead. An engineering compromise was proposed whereby the electrodes would be oriented on opposite sides of the lead and spaced from each other along the length of the lead. The selected spacing would be within a statistically expected range such that a wavefront, approching the electrodes along the line connecting the two electrodes, would be expected to pass over the electrodes such that the negative and positive maxima would reach different electrodes at about the same time.

Although the Brownlee lead is an improvement over the Goldreyer lead, the lead is still very dependent upon the direction of an approaching wavefront. It is still possible for a wavefront to approach the two electrodes from along a direction perpendicular to a line connecting those electrodes. Such an occurrence would still result in little or no difference by the electrodes. This effect is, of course, greatest in the case of the perpendicular approaching wavefront, but the effect is also experienced in any wavefront that does not advance along the line connecting the two electrodes.

It is an object of my invention, therefore, to provide a cardiac pacemaker electrode which is less sensitive to the direction of approaching wavefronts.

It is also an object of my invention to provide such a lead which can be easily inserted transvenously into the heart. A further object of my invention is to provide such a lead which does not significantly impede the flow of blood through the heart.

Another object of my invention is to provide an bipolar lead which can be optimized for expected approaching wavefronts.

SUMMARY OF MY INVENTION

I have invented a bipolar sensing lead for use with a implantable device, particularly a cardiac pacemaker, comprising a first sensing electrode located adjacent an outer surface of the lead and a second sensing electrode spaced away from that surface. In my preferred embodiment, the first sensing electrode is a ring electrode at the outer surface of the lead. The second sensing electrode comprises a conductive ring around the circumference of a collapsible, flexible disk. Preferably the disk is comprised of the same material as an insulating outer sheath of the lead. Polyurethane or silicone rubber are known materials for such applications. The conductive ring is comprised of a flexible conductive material such as a conductive polymer, conductive film, or thermoplastic composite such as graphite. Alternatively, the conductive ring may be replaced by electrically connected segments, thereby permitting solid conductor material to be used while continuing to allow the ring to be collapsed for passage through a vein or a heart valve during implant or explant of the lead. The flexible disk may be perforated to reduce resistance to blood flow through the heart chamber.

Other objects and features of my invention will be apparent to those skilled in the art from the following detailed description of my preferred embodiments made with reference to the accompanying drawings.

BRIEF DESCRIPTION OF THE DRAWINGS

FIGS. 10-15 are alternative embodiments of the collapsible electrode of my present invention.

DETAILED DESCRIPTION OF MY PREFERRED EMBODIMENT

Figure 1:
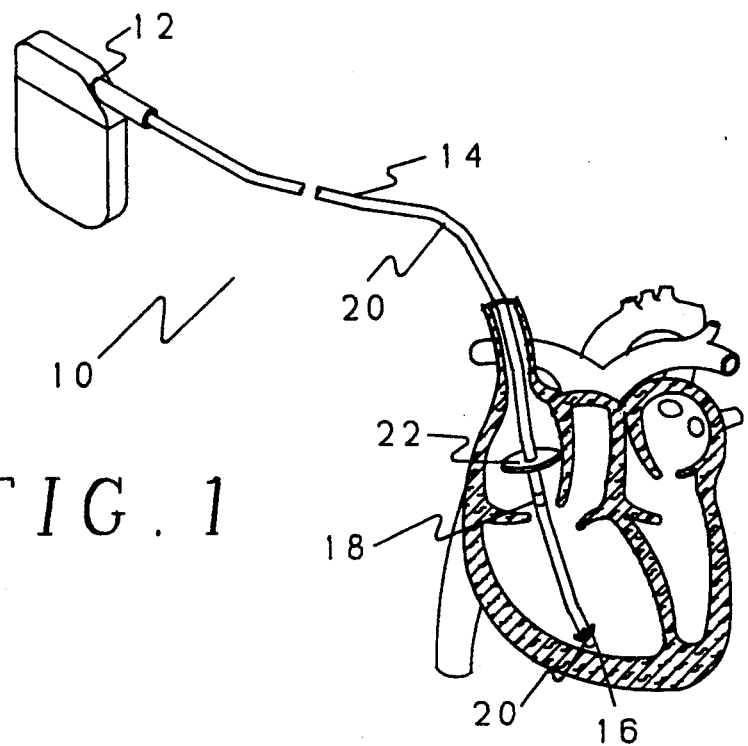
FIG. 1 is perspective view of a cardiac pacemaker system according to my present invention with a cardiac pacemaker and a lead, showing placement of the lead in a cut away section of a human heart.

I will now describe my preferred embodiment of my invention. In referring to the accompanying figures, like numerals will be used to refer to like parts throughout this description. In FIG. 1, a cardiac pacemaker system, generally designated 10, is shown in perspective view. A cardiac pacemaker 12 is provided having the capacity to sense electrical artifacts with at a least two sense electrodes and to provide a stimulus through a pacing electrode. As is known in the art, one of the sensing electrodes and the stimulating electrode may be the same structure. A lead 14 is shown connected to the pacemaker 12. In my preferred embodiment, the lead comprises a stimulating electrode 16 at a distal end of the lead. As is known in the art, fixation means should generally be provided. I have illustrated tines 20. Spaced away from the stimulating electrode 16 is the ring sense electrode 18. I prefer to use a standard ring-type electrode for this sense electrode, but other configurations may be adopted by those skilled in the art without departing from the spirit or teachings of my invention. For example, an electrode might be selected which does not completely surround the lead. In general, however, the ring sense electrode 18 should be relatively close to the outer surface of the lead. Spaced from the ring electrode 18 is a collapsible electrode 22. Together with the ring electrode 18, the collapsible electrode 22 forms a bipolar pair of electrodes for sensing electrical wavefronts in the heart.

Figure 2:
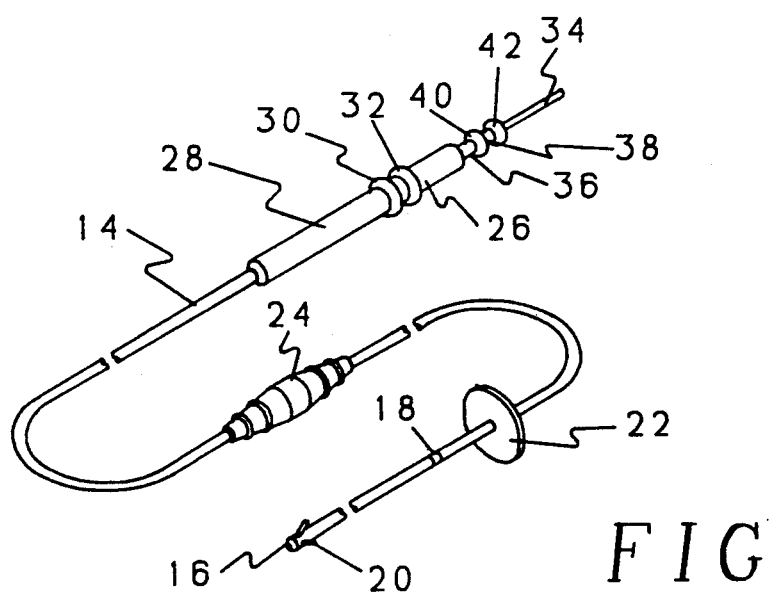
FIG. 2 is a perspective view of the lead of FIG. 1.

The structure of the lead 14 can be seen in more detail in FIG. 2. In addition to the structure heretofore identified, certain conventional features should also be provided such as, for example, a suture sleeve 24. At the proximal end 26 of the lead, a connector 28 is provided for insertion into the cardiac pacemaker 12. The connector 28 may have sealing rings 30, 32 to prevent body fluids from entering into the connection between the pacemaker 12 and the lead 14. A stimulator connector 34 should be provided for receiving electrical stimuli from the pacemaker and conducting those stimuli, through a coiled conductor, to the stimulating electrode 16. In addition, one or more sensor contacts 36, 38 should be provided for conducting electrical signals from the sense electrodes 18, 22 to the pacemaker 12. As mentioned above, the stimulating electrode 16 and one of the sense electrodes may be the same structure. In that case, the stimulator connector 34 can serve dual functions. These electrodes should be separated, as is known in the art, by seals 40, 42 to prevent electrical cross talk.

A single connector 28 is shown as my preferred embodiment. It is known, however, to provide a single pass lead with two proximal connectors, one for atrial connections and one for ventricular connections. This permits a single pass lead to be used with a pacemaker which is configured to receive dual leads with one lead for the atrium and one for the ventricle. Such a configuration is well known in the art.

Figure 3:
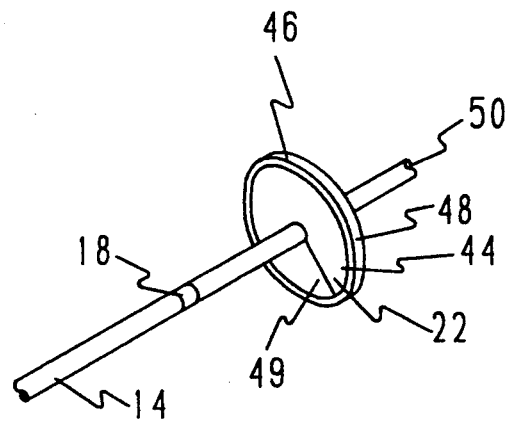
FIG. 3 is a perspective view of bipolar sense electrodes of the lead of FIG. 1.
Figure 4:
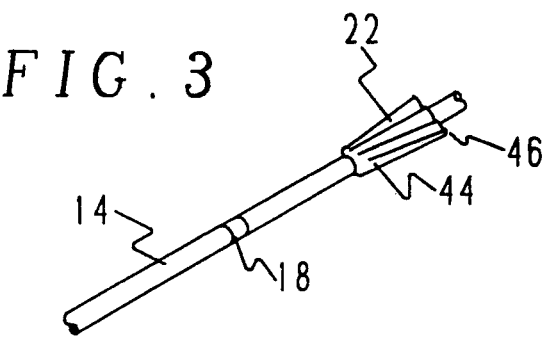
FIG. 4 is a perspective view of the electrodes of FIG. 3 with a collapsible sense electrode collapsed around the lead for insertion into the heart.

The bipolar sense electrodes of my invention are illustrated in perspective view in FIGS. 3 and 4. The collapsible electrode 22 comprises a flexible disk 44 through which the lead 14 passes. A flexible peripheral conductor 46 surrounds an outer edge 48 of the flexible disk 44. The peripheral conductor 46 is connected by a conductor 49 to a coil conductor 50 inside the lead and the coil conductor 50 is connected to the sensor contact 38 at the proximal end of the lead 14.

Figure 5:
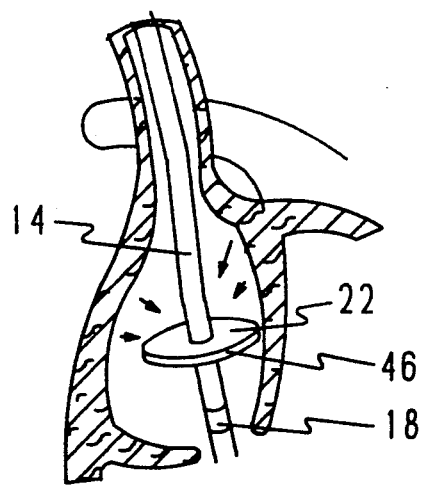
FIG. 5 is a cut away view of an atrial chamber of the human heart showing a portion of the lead with the bipolar electrodes.

As can be seen in FIG. 4, to insert the lead 14 into the heart, the collapsible sense electrode 22 is folded around the lead 14. Once within the heart, the collapsible sense electrode 22 will unfold and extend so that the peripheral conductor 46 is deployed away from the lead 14. In this configuration, the two sense electrodes 18, 22 are capable of detecting approaching wavefronts which pass over the sense electrodes in the heart. Such wavefronts may approach from many directions, as indicated by the arrows in FIG. 5. A lead with sense electrodes according to my present invention is capable of detecting characteristics of wavefronts approaching from any direction in at least a hemispherical region without significant loss of sensitivity.

Figure 6:
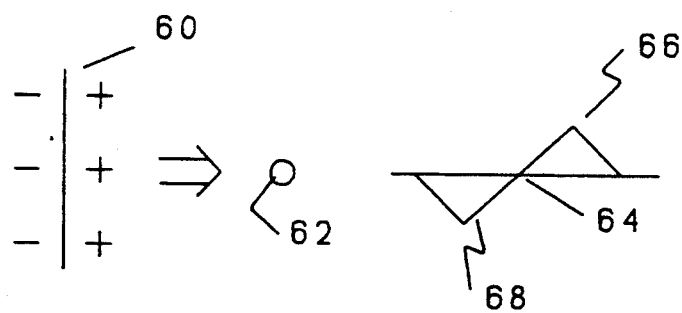
FIG. 6 is a schematic representation of a wavefront passing over a single electrode.
Figure 7:
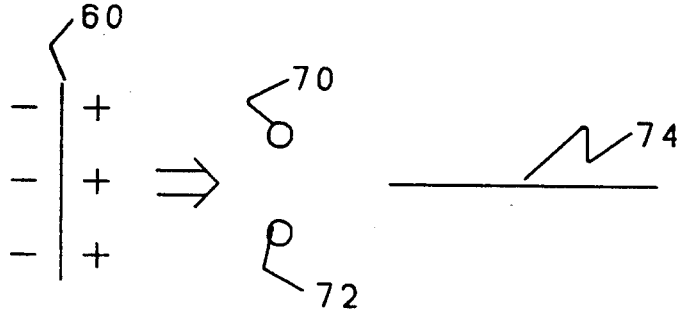
FIG. 7 is a schematic representation of a wavefront passing over bipolar electrodes in a direction perpendicular to a line connecting the two electrodes.
Figure 8:
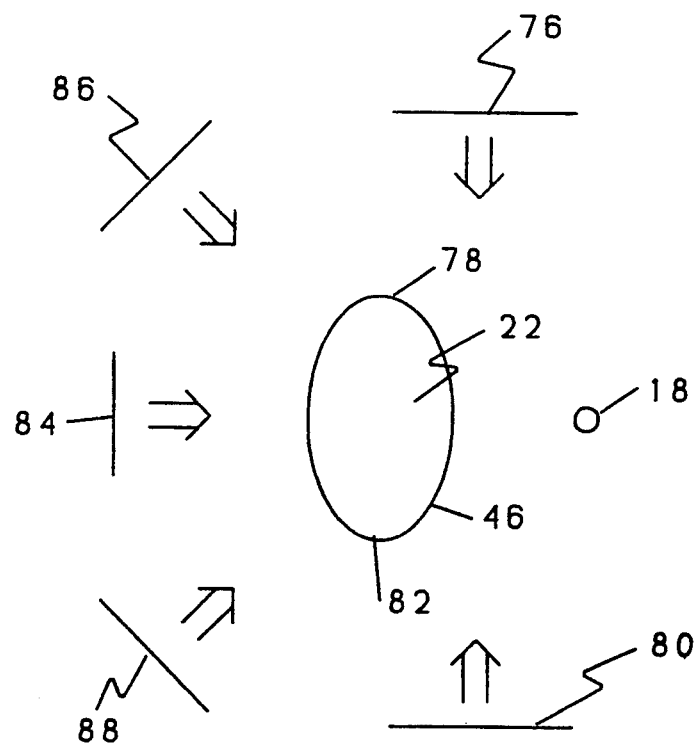
FIG. 8 is a schematic representation of a plurality of wavefronts approaching an electrode configuration according to my present invention.

To explain the principles of my invention, I refer the reader to the diagrams of FIGS. 6-9. FIG. 6 is a schematic representation of an electric dipole wavefront 60 approaching a point electrode 62. A graph 64 represents the electrical status sensed by the electrode 62. As the wavefront approaches the electrode, there is an increase in positive potential until a positive maximum 66 is reached. The positive potential then declines relatively rapidly, passes through zero and becomes increasingly negative to a negative maximum 68 as the negative part of the wavefront passes over the electrode 62. The potential at the electrode then declines more or less to ground state. In bipolar electrodes, the electrical conditions of two locations are sensed simultaneously and the difference is compared inside the pacemaker. It is possible to detect the negative maximum 68 and the positive maximum 66 simultaneously, thus increasing the chances that a wavefront will be accurately identified. However, it is possible, as shown in FIG. 7, that a wavefront 60 may approach bipolar electrodes 70, 72 along the path perpendicular to a line connecting the two electrodes. Should that occur, the measured difference in electrical potential between the electrodes 70, 72 will be zero as represented by the straight line 74.

This situation is avoided by using sense electrodes according to my invention. As illustrated diagrammatically in FIG. 8, the ring electrode 18 and the collapsible electrode 22 can be approached by wavefronts throughout the hemispherical area as shown without significant loss of sensitivity. For example, if an upper wavefront 76 approaches the two electrodes, the wavefront will encounter an upper edge 78 of the collapsible electrode before it passes over the ring electrode 18. A lower wavefront 80 approaching the two electrodes will encounter a lower edge 82 of the collapsible electrode 40 before reaching the ring electrode 18. A wavefront 84 propagating from left to right in FIG. 8, would encounter all of the collapsible electrode 22 before reaching the ring electrode 18. In all cases between these extremes, for example, with wavefronts 86, 88, the wavefronts will arrive at the collapsible electrode before reaching the ring electrode.

The reader will note that there can be a wavefront which approaches perpendicular to a line connecting the ring electrode 18 and the edge 48 of the collapsible electrode 22 which will arrive simultaneously at the ring electrode and the edge of the collapsible electrode. If the collapsible electrode were a point electrode, the zeroing condition explained in connection with FIG. 7 above would be observed. Because of the increased dimension of the collapsible electrode, a signal will still be detected similar to that detected by a single point sense electrode. Thus, there is a region where sensitivity of the electrodes to approaching wavefronts is reduced, but not eliminated. Wavefronts which are approaching the electrodes from the ring electrode side and which are parallel to the surface of an imaginary cone with its apex at the ring electrode and base at the collapsible electrode will not be detected as well. This direction of reduced sensitivity can be adjusted by varying the spacing between the ring electrode 18 and the collapsible electrode 22 and by varying the diameter of the collapsible electrode. In an application within the heart, it is expected that an electrical phenomenon in the atrium would usually commence in the sinus node and propagate from the upper part of the heart toward the ventricle of the heart. It is generally desired to detect these so-called "P" waves in preference to reverse propagation of "R" waves from the ventricle. It is therefore advantageous to sense relatively uniformly for waves that propagate from the upper hemisphere and to discriminate against waves which originate in the lower hemisphere.

Figure 9:
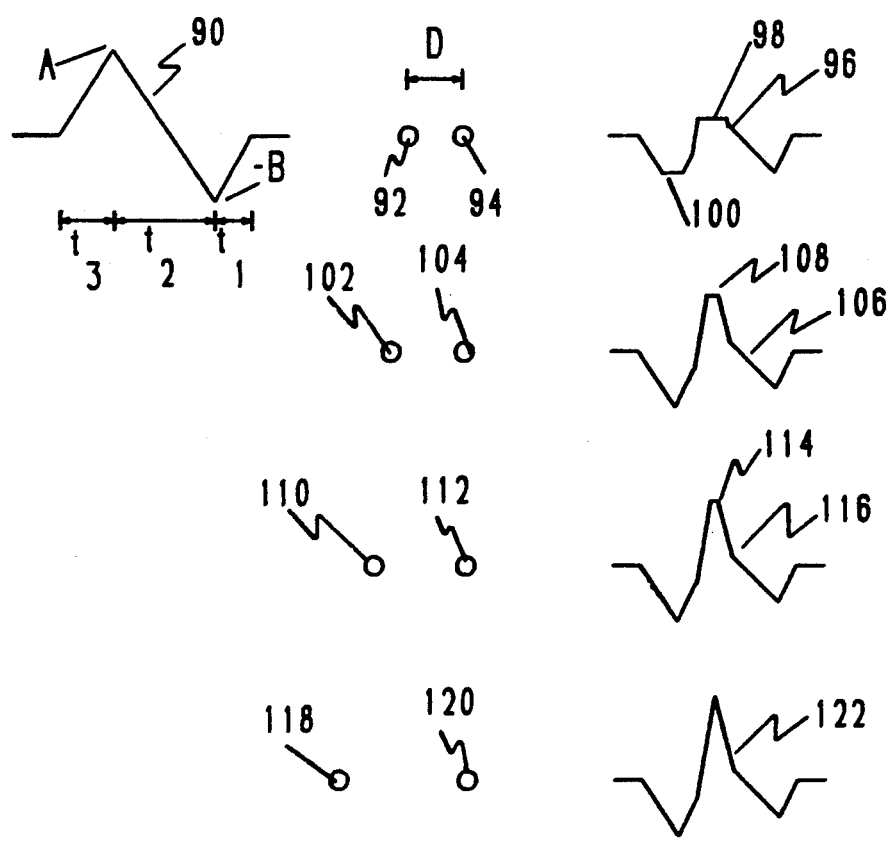
FIG. 9 is a schematic representation of the effect of spacing in sensing with bipolar electrodes.

FIG. 9 illustrates another design parameter important in developing bipolar sense electrodes. A wavefront 90 is diagrammatically indicated and may be assumed to be traveling from left to right toward bipolar electrodes 92, 94. These electrodes 92, 94 are separated by a distance "D". The wavefront 90 is traveling at some velocity through the cardiac tissue and blood in the heart. The wavefront 90 can, therefore, be divided into areas dependent on the time it takes for each part of the wavefront to reach a selected point. In a first time period $t_1$, the wavefront becomes increasingly negative to a negative maximum, $-B$. During the second time period $t_2$, the electrical potential increases to a positive maximum A. During a third time period $t_3$, the electrical potential falls. It will be apparent that bipolar electrodes 92, 94 will detect a difference in electrical potential with respect to the pacer case between the two electrodes as the wavefront 90 sweeps across the electrodes. This potential difference is approximately represented by graph 96. Because the difference between electrode 92 and electrode 94 is being detected, the graph 96 does not duplicate the wavefront 90. Moreover, since electrodes 92, 94 are spaced by a distance "D" there is a clipping effect represented at 98 and 100 because the respective maximums $-B$ and A will not reach the two electrodes at the same time. This effect is progressively illustrated in the succeeding portions of FIG. 9. If electrodes 102 and 104 are spaced slightly further apart than electrodes 92, 94 the associated graph 106 displays one clipped area 108. If electrodes 110, 112 are spaced yet further apart, clipping in 114 in graph 116 diminishes yet further. If electrodes 118, 120 are spaced a critical distance apart, a full maximum difference will detected as shown in graph 122. It will be apparent, however, that if the electrodes are spaced further than the critical distance apart, sensitivity is again lost.

It is impossible to specify universally a critical distance for the spacing of bipolar sense electrodes. It is well known in the medical art, that the human body is subject to significant variations. Moreover, a wavefront can be expected to approach the electrodes from any of a number of directions, as explained above. With this variation in speed and direction, a universal critical distance cannot be specified. The designer of a bipolar sense electrode must, however, seek an appropriate compromise and obtain a suitable range for detection purposes. It will be noted that a bipolar sense electrode constructed in accordance with the principles of my invention will present a range of distances "D" between the ring electrode 18 and points on the flexible conductive electrode on the collapsible electrode 22. It may be expected, therefore, that a bipolar electrode according to my invention will be less sensitive to variations in the critical distance "D".

Figure 10:
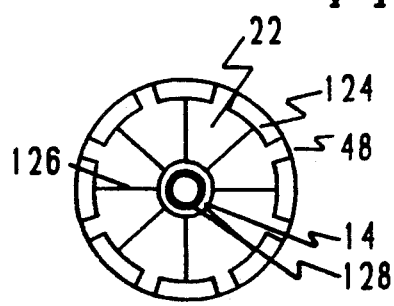

I will now describe some alternative configurations for the collapsible electrode 22 of my invention. FIG. 10 shows the collapsible electrode 22 having a plurality of spaced peripheral electrodes 124. Each of the peripheral electrodes 124 is symmetrically placed around the edge 48 of the collapsible electrode 22, and each is connected by a conductor 126 to the lead 14. Within the lead 14 a coil conductor 128, connected to the conductors 126, carries electrical signals to the pacemaker, as described above.

Figure 11:
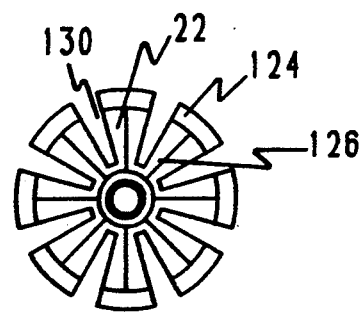

A similar configuration is shown in FIG. 11. The peripheral electrodes 124 and conductors 126 are similar to the embodiment of FIG. 10, but the collapsible electrode 22 is also provided with slots 130 between the electrodes. This permits somewhat greater flexibility in the collapsible electrode 22 and also increases the possible flow of blood past the electrode.

Figure 12:
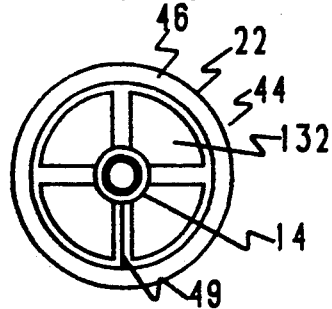

Another embodiment is illustrated in FIG. 12. The peripheral conductor 46 is used on the collapsible sense electrode 22 and the single conductor 49 is provided. Areas of the flexible disk 44, however, are cut away to leave gaps 132 to decrease the resistance to flow of blood.

Figure 13:
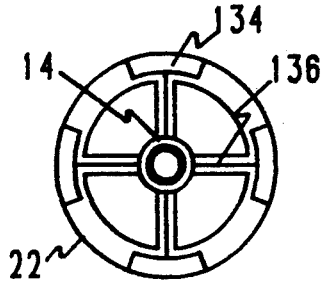

The configuration of FIG. 12 may be also be modified, as shown in FIG. 13, to use multiple peripheral electrodes 134, each with individual conductors 136. In FIG. 13, four electrodes 134 are shown but it will be recognized that more conductors could be used or that the electrodes 134 could subtend greater arcs around the edge of the collapsible sense electrode 22. In general, I recommend no fewer than three peripheral electrodes be employed.

FIG. 14 illustrates another embodiment of the collapsible electrode. In this embodiment, the lead 14 is surrounded by a plurality of tines 140 each of which has conductive tip 142. Each tip 142 is connected through an electrical conductor 144 to a common coil conductor. Tines are known in the art of cardiac pacing leads and are described in such patents as U.S. Pat. No. 3,902,501 to Citron, et al. and U.S. Pat. No. 4,722,353 to Sluetz. In these patents, however, the tines are employed as fixation apparatus.

FIG. 15 illustrates an additional embodiment of my invention. This embodiment is similar to the principal embodiment illustrated in FIG. 3 above but includes the additional element of a ring electrode 146 located on the lead 14. The ring electrode 146 is electrically connected to the peripheral conductor 46. This configuration permits more sensitive identification of wavefronts approaching the bipolar sense electrodes along a line parallel to the axis of the lead 14.

It will be apparent to those skilled in the art that my invention can be embodied in other configurations without departing from the teachings or essential characteristics thereof. The foregoing description is, therefore, to be considered illustrative and not restrictive and the scope of my invention is to be defined by the following claims. All changes or variations that would come within the meaning of equivalency of the claims are intended to be incorporated therein.

I claim as my invention:

1. A lead for a therapeutic device comprising
a lead body having a proximal end, a distal end and an outside surface, said proximal end being adapted to be connected to said therapeutic device;
at least one stimulating electrode for conducting electrical pulses to a ventricle of a human heart to be stimulated, said stimulating electrode being connected electrically to said proximal end through said lead body,
a first sensing electrode located substantially on said outer surface of said lead body in an atrium of said human heart and connected electrically to said proximal end of said lead body;
a second sensing electrode displaced proximally from said first sensing electrode along said lead body in said atrium and connected electrically to said proximal end of said lead body; and
a flexible elastomeric sheet perforated with at least one hole attached to said lead body for supporting said second electrode outwardly from said lead body and capable of collapsing against the outer surface of the lead body.

2. The lead according to claim 1 wherein said second sensing electrode comprises a conductive ring.

3. The lead according to claim 1 wherein the second electrode comprises a plurality of electrodes, each of said plurality of electrodes being spaced from each other and spaced outwardly from the outer surface of said lead body.

4. A cardiac pacemaker system adapted to detect the electrical condition of a human heart in at least the right atrium of said heart and to stimulate said heart in at least the right ventricle thereof, said cardiac pacemaker system comprising:
a cardiac pacemaker adapted to process electrical signals representative of the electrical condition of at least the atrium and to produce stimulating pulses in response thereto,
a lead having
a lead body having a proximal end, a distal end and an outside surface, said proximal end being adapted to be connected to said cardiac pacemaker;
at least one stimulating electrode for conducting said stimulating pulses to said right ventricle of said human heart, said stimulating electrode being connected electrically to said proximal end through said lead body,
a first sensing electrode located substantially on said outer surface of said lead body in said right atrium of said human heart and connected electrically to said proximal end of said lead body;
a second sensing electrode displaced proximally from said first sensing electrode along said lead body and connected electrically to said proximal end of said lead body; and
means attached to said lead body for supporting said second electrode outwardly from said lead body.

5. The cardiac pacemaker system according to claim 4 wherein said second sensing electrode comprises a conductive ring.

6. The cardiac pacemaker system according to claim 4 wherein the supporting means further comprises means for collapsing said second electrode against the outer surface of the lead body.

7. The cardiac pacemaker system according to claim 6 wherein the supporting means comprises a flexible elastomeric sheet.

8. The cardiac pacemaker system according to claim 7 wherein the elastomeric sheet is perforated with at least one hole.

9. The cardiac pacemaker system according to claim 8 wherein the second electrode comprises a plurality of electrodes, each of said plurality of electrodes being spaced from each other and spaced outwardly from the outer surface of said lead body.

10. The cardiac pacemaker system according to claim 4 wherein the second electrode comprises a plurality of electrodes, each of said plurality of electrodes being spaced from each other and spaced outwardly from the outer surface of said lead body.

11. The cardiac pacemaker system according to claim 10 wherein the supporting means comprises a plurality of supporting means, each supporting means being associated with one of said plurality of electrodes.

12. A lead for a therapeutic device comprising
a lead body having a proximal end, a distal end and an outside surface, said proximal end being adapted to be connected to said therapeutic device;
at least one stimulating electrode for conducting electrical pulses to a human organ to be stimulated, said stimulating electrode being connected electrically to said proximal end through said lead body,
a first sensing electrode located substantially on said outer surface of said lead body and connected electrically to said proximal end of said lead body;
a second sensing electrode displaced from said first sensing electrode along said lead body and connected electrically to said proximal end of said lead body; and
a flexible elastomeric sheet perforated with at least one hole for supporting said second electrode outwardly from said lead body, said elastomeric sheet being collapsible against the outer surface of the lead.

13. The lead according to claim 12 wherein the second electrode comprises a plurality of electrodes, each of said plurality of electrodes being spaced from each other and spaced outwardly from the outer surface of said lead body.

14. A cardiac pacemaker system adapted to detect the electrical condition of a human heart in at least the right atrium of said heart and to stimulate said heart in at least the right ventricle thereof, said cardiac pacemaker system comprising:
a cardiac pacemaker adapted to process electrical signals representative of the electrical condition of at least the atrium and to produce stimulating pulses in response thereto,
a lead having
a lead body having a proximal end, a distal end and an outside surface, said proximal end being adapted to be connected to said cardiac pacemaker;
at least one stimulating electrode for conducting said stimulating pulses to said human heart, said stimulating electrode being connected electrically to said proximal end through said lead body,
a first sensing electrode located substantially on said outer surface of said lead body and connected electrically to said proximal end of said lead body;
a second sense electrode displaced from said first sense electrode along said lead body and connected electrically to said proximal end of said lead body; and
a flexible elastomeric sheet perforated with at least one hole for supporting said second electrode outwardly from said lead body, said elastomeric sheet being collapsible against the outer surface of the lead.

15. The cardiac pacemaker system according to claim 14 wherein the second electrode comprises a plurality of electrodes, each of said plurality of electrodes being spaced from each other and spaced outwardly from the outer surface of said lead body.

* * * * *